United States Patent
Dahlberg et al.

(10) Patent No.: US 10,687,983 B2
(45) Date of Patent: Jun. 23, 2020

(54) WOUND PAD

(71) Applicant: MÖLNLYCKE HEALTH CARE AB, Gothenburg (SE)

(72) Inventors: Anders Dahlberg, Olofstorp (SE); Carianne Nilsson, Lerum (SE); Magnus Paledzki, Brunswick, ME (US); Johan Uveborn, Askim (SE)

(73) Assignee: Mölnlycke Health Care AB, Göteborg (SE)

( * ) Notice: Subject to any disclaimer, the term of this patent is extended or adjusted under 35 U.S.C. 154(b) by 1283 days.

(21) Appl. No.: 14/785,180

(22) PCT Filed: Apr. 17, 2014

(86) PCT No.: PCT/EP2014/057969
§ 371 (c)(1),
(2) Date: Oct. 16, 2015

(87) PCT Pub. No.: WO2014/170461
PCT Pub. Date: Oct. 23, 2014

(65) Prior Publication Data
US 2016/0128872 A1  May 12, 2016

Related U.S. Application Data

(60) Provisional application No. 61/812,986, filed on Apr. 17, 2013.

(51) Int. Cl.
*A61F 13/531* (2006.01)
*A61F 13/00* (2006.01)
(Continued)

(52) U.S. Cl.
CPC .. *A61F 13/00029* (2013.01); *A61F 13/00068* (2013.01); *A61F 13/0216* (2013.01);
(Continued)

(58) Field of Classification Search
CPC .......... A61F 13/00217; A61F 13/00017; A61F 13/00038; A61F 13/00046;
(Continued)

(56) References Cited

U.S. PATENT DOCUMENTS

2005/0209574 A1* 9/2005 Boehringer ............. A61F 13/36
604/289
2010/0036334 A1 2/2010 Heagle et al.
(Continued)

FOREIGN PATENT DOCUMENTS

EP  2 545 943  1/2013
GB  886474  1/1962
(Continued)

OTHER PUBLICATIONS

International Search Report from the European Patent Office for International Application No. PCT/EP2014/057969, dated Sep. 30, 2014.
(Continued)

*Primary Examiner* — Anna K Kinsaul
*Assistant Examiner* — Camtu T Nguyen
(74) *Attorney, Agent, or Firm* — Finnegan, Henderson, Farabow, Garrett & Dunner LLP

(57) ABSTRACT

Wound pads and systems and kits comprising wound pads whose total thickness can be modified by a user without the use of tools, comprising a plurality of separable layers having layer thicknesses less than the thickness of the wound pad. The wound pads may be used as wound fillers in the context of negative pressure wound therapy (also known as "vacuum treatment", "reduced pressure" treatment).

24 Claims, 9 Drawing Sheets

(51) Int. Cl.
- *B32B 7/06* (2019.01)
- *B32B 7/12* (2006.01)
- *A61F 13/02* (2006.01)
- *B32B 3/26* (2006.01)
- *B32B 5/18* (2006.01)
- *B32B 7/08* (2019.01)
- *A61M 1/00* (2006.01)

(52) U.S. Cl.
CPC ........... *A61M 1/0088* (2013.01); *B32B 3/266* (2013.01); *B32B 5/18* (2013.01); *B32B 7/06* (2013.01); *B32B 7/08* (2013.01); *B32B 7/12* (2013.01); *A61F 2013/00553* (2013.01); *A61F 2013/00557* (2013.01); *A61F 2013/00842* (2013.01); *B32B 2250/22* (2013.01); *B32B 2266/025* (2013.01); *B32B 2266/0221* (2013.01); *B32B 2266/0264* (2013.01); *B32B 2266/0278* (2013.01); *B32B 2266/06* (2013.01); *B32B 2307/728* (2013.01); *B32B 2307/73* (2013.01); *B32B 2556/00* (2013.01)

(58) Field of Classification Search
CPC .. A61F 13/00068; A61F 13/14; A61F 13/148; A61F 13/15; A61F 2013/00021; A61F 2013/00157; A61F 5/03; A61F 2013/00217; A61M 27/00
See application file for complete search history.

(56) References Cited

U.S. PATENT DOCUMENTS

| | | | |
|---|---|---|---|
| 2010/0179515 A1* | 7/2010 | Swain | A61B 17/11 604/543 |
| 2011/0112492 A1* | 5/2011 | Bharti | A61M 1/0088 604/319 |
| 2011/0213287 A1 | 9/2011 | Lattimore et al. | |
| 2012/0041402 A1* | 2/2012 | Greener | A61F 13/00068 604/319 |
| 2012/0315421 A1* | 12/2012 | Kuo | B42D 5/003 428/40.2 |
| 2014/0163447 A1 | 6/2014 | Wieland et al. | |

FOREIGN PATENT DOCUMENTS

| WO | WO 2010/092334 A1 | 8/2010 |
|---|---|---|
| WO | WO 2011/106722 A1 | 9/2011 |
| WO | WO 2013/086426 | 6/2013 |

OTHER PUBLICATIONS

Written Opinion of the International Searching Authority from the European Patent Office for International Application No. PCT/EP2014/057969, dated Sep. 30, 2014.

* cited by examiner

WOUND PAD

This application is a U.S. National stage application of PCT/EP2014/057969 filed Apr. 17, 2.014 that claims priority to U.S. Provisional Application 61/812,986 filed Apr. 17, 2013, the disclosure of each application is incorporated herein by reference.

BACKGROUND

Some wounds, such as pressure or diabetic ulcer wounds, or surgically created wounds, form a cavity in a patient's body and are often called "cavity wounds." It can be desirable to fill the wound cavity, e.g., as part of a course of treatment. Various types of wound dressings or pads are used to fill wound cavities. These wound dressings or pads must be fitted for the particular wound size and shape, which can vary greatly. Some such dressings are easily conformable to the size and shape of the particular wound being treated. For example, gauze may be used as a cavity wound filler. As a further example, MELGISORB™ (produced by Mölnlycke Health Care) is a soft, sterile calcium sodium alginate dressing that is used to pack wound cavities.

In some wound care contexts, it can be desirable to use a wound pad made of a more rigid material. For example, porous and semi-rigid polymer foams are often used as wound fillers during negative pressure wound treatment. These materials may offer the advantage of allowing fluid channels through themselves and maintaining a relatively uniform open structure even when subjected to negative pressure. Without wishing to be bound by any particular theory, it is also thought that the mechanical interaction between these more rigid materials and the wound may contribute to wound healing processes.

These more rigid dressings or pads can be difficult to size and shape to fit a wound. Such pads are typically supplied in one of several standard sizes and shapes, which then must be individually altered, typically with utensils or tools such as scissors and/or a scalpel. The process of individually shaping and sizing a wound pad can be messy, time-consuming, and/or frustrating to the clinician and/or patient.

The present disclosure is directed at overcoming one or more of these or other shortcomings in the art.

SUMMARY

The present disclosure relates to wound pads that can be used, for example, as fillers in wound cavities, as well as systems comprising such wound pads and methods for using such wound pads. In some embodiments, the wound pads are used as wound fillers in the context of negative pressure wound therapy (also known as "vacuum treatment", or "reduced pressure" treatment).

Wound cavities are of differing shapes and sizes. During use, a pre-supplied wound pad is often cut by a clinician in order to fit it to the specific wound being treated using tools such as scissors. This process can be cumbersome and messy. For example, bits of material and other debris from the wound pad are often generated as a result of using tools such as scissors to shape and size the wound pad. Moreover, while it may be somewhat feasible to modify the length and width of a pre-supplied wound pad, it may be especially difficult for a user to modify the thickness, for example, when the wound pad is substantially planar in shape, e.g., having a thickness that is significantly less than either its length or width. And, even if the thickness is modifiable, doing so may generate a substantial amount of debris, which can be detrimental in a treatment environment. Furthermore, modifying a wound pad to a particular shape and/or desired thickness so it is adequately sized for a particular wound with utensils or tools may require substantial skill by the clinician or may generate considerable waste if a mistake is made to one pad and a clinician must retry with a new pad.

Supplying wound pads in the form of multiple thinner wound pads could potentially ameliorate this difficulty. Nevertheless, as recognized by the present inventors, packaging such multiple wound pads into a kit, e.g. a wound dressing kit, may be cumbersome. Moreover, supplying multiple, relatively thinner pads may not be an adequate option when a relatively thicker pad is desired for a particular wound.

The present disclosure provides, among other things, a solution to the aforementioned problems. Described herein are wound pads whose total thickness can be modified by a user without the use of tools and that are furthermore easy to package (e.g., can be included in a kit as a single piece). Disclosed wound pads comprise single contiguous units having a plurality of separable layers. Also disclosed are negative pressure wound therapy systems comprising such wound pads, kits including such wound pads, and methods of using such wound pads.

BRIEF DESCRIPTION OF THE DRAWING

FIGS. 4A and 4B show exemplary configurations in which a first region connected to at least one adjacent layer is surrounded by a second region unconnected to any adjacent layer. FIGS. 4C and 4D show exemplary configurations in which a first and third region, each connected to at least one adjacent layer, are surrounded by a second region unconnected to any adjacent layer.

FIG. 7A depicts a top view of a single piece of material cut or otherwise shaped into three similarly shaped and sized sections and folded as depicted in FIG. 7B to form a wound pad having three separable layers, a side view of which is shown in FIG. 7C.

DEFINITIONS

Figure 1:
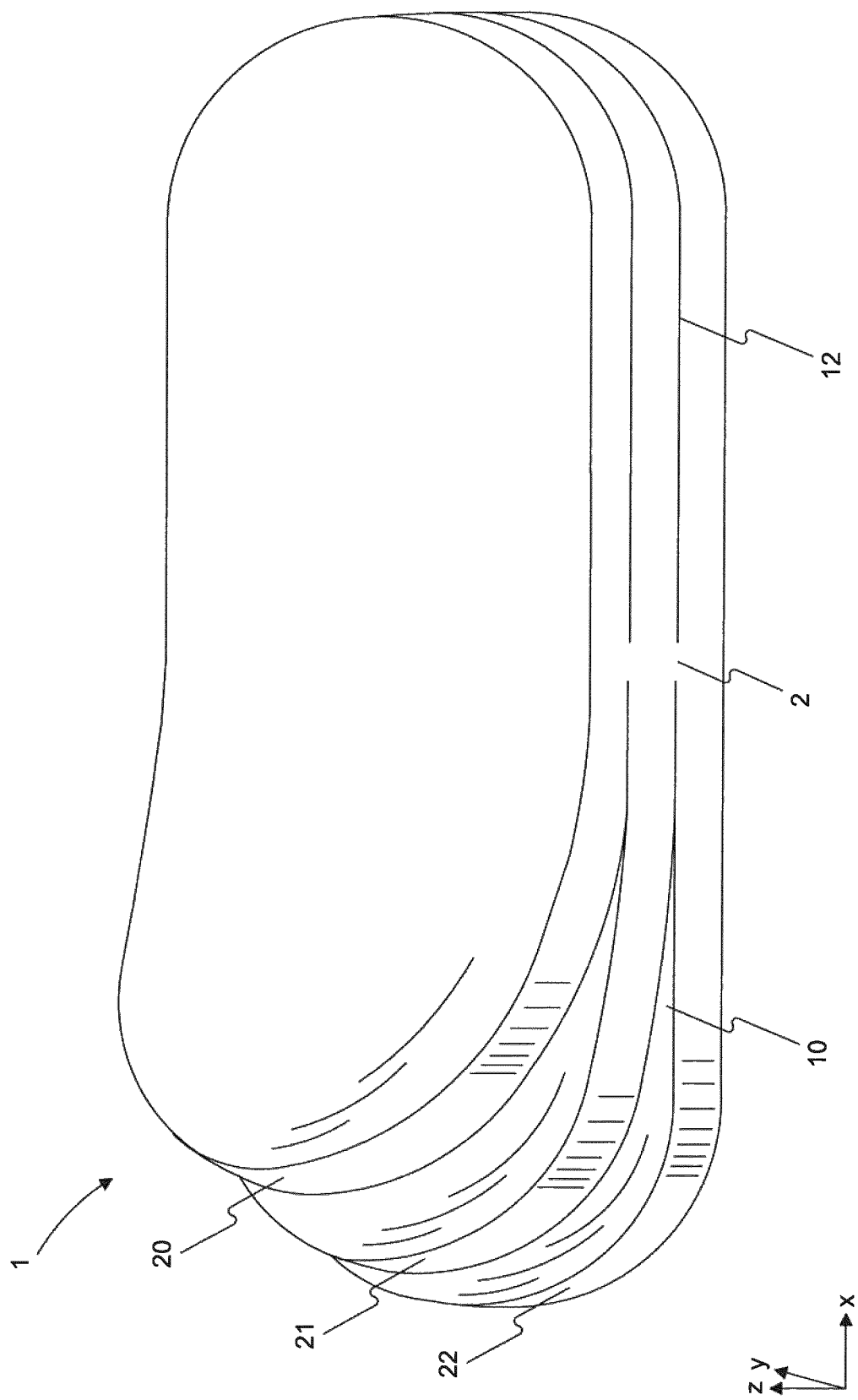
FIG. 1 depicts a perspective of an exemplary wound pad having three separable layers.

As used herein, the terms "about" or "approximately," refer to, for example, a number or percentage, generally including numbers that fall within a range of 5%, 10%, or 20% in either direction (plus or minus) of the number unless otherwise stated or otherwise evident from the context (except where such a number would be physically impossible, e.g. exceed 100% of a possible value or fall below 0% of a possible value).

As used herein, the term "connected region" refers to a region between two or more sections of an object, e.g., a wound pad, that is connected. For example, a connected region may be formed by cutting a homogeneous block to form two or more layers that remain consanguineous with one another at the connected region, i., not having been cut at all. Alternatively or additionally, a connected region may be formed by joining of two formerly separate pieces together.

As used herein, the term "consanguineous" refers to a characteristic of an object in that the object is constructed from a single piece of material, and therefore also made entirely of the same material throughout, i.e., a homogeneous object. As a non-limiting example, a wound pad that is shaped and cut from a single, homogeneous block of foam material would be considered a "consanguineous" wound pad.

As used herein, the term "homogeneous" refers to the property of an object having a uniform material composition throughout. Homogeneous objects may or may not be consanguineous.

As used herein, the term "hydrophilic" refers to the water-permeability property of a material or the water-attracting property of a molecule. In the context of a material with pores (such as, for example, open-cell foams) or materials with through-holes, such a material is "hydrophilic" if the material wicks up water. In the context of a material without pores or any through-holes, such a material is considered "hydrophilic" if it does not resist the flow of water into or through the material. For example, hydrophilicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

As used herein, the term "hydrophobic" refers to the water-impermeability property of a material or the water-repelling property of a molecule. In the context of a material with pores (such as, for example, open-cell foams) or materials with through-holes, such a material is "hydrophobic" if the material does not wick up water. In the context of a material without pores or any through-holes, such a material is considered "hydrophobic" if it resists the flow of water into or through the material. For example, hydrophobicity of a material can be tested using a water column of up to one inch height exerting pressure on the material for at least 60 minutes, at least 90 minutes, or at least 24 hours. By "resisting," it is meant that any flow of water into or through the foam in such a test is below a detection limit for the test.

As used herein, the term "length" has its ordinary meaning as used in the art. Unless otherwise indicated, when a Cartesian coordinate system is used, the length of an object is measured along the x-axis. Unless otherwise indicated, in the case of objects that would not be considered to have a uniform length, the length is measured at the longest part of the object. For example, for a solid object having an oblong cross-section, one would measure the length at the midpoint of the width of the object (i.e., where the object is the longest).

As used herein, the terms "negative pressure," "vacuum," "suction," "reduced pressure," and "subatmospheric" are used interchangeably and all refer to pressure below normal atmospheric pressure.

As used herein, the term "sterilized" refers to 1) the state of being substantially free of living microorganisms, or 2) being subject to a process in order to be substantially free of living microorganisms.

As used herein, the term "substantially" refers to a complete or nearly complete extent or degree of an action, characteristic, property, state, structure, item, or result. The exact allowable degree of deviation from absolute completeness may in some cases depend on the specific context. One of ordinary skill in the art will understand, for example, that "substantially the same" refers to two characteristics or values that are either equal or close enough within acceptable tolerances.

As used herein, the term "thickness" has its ordinary meaning as used in the art. Unless otherwise indicated, when a Cartesian coordinate system is used, the thickness of an object is measured along the z-axis. Unless otherwise indicated, in the case of objects that would not be considered to have a uniform thickness, the thickness is measured at the thickest part of the object.

As used herein, the term "width" has its ordinary meaning as used in the art. Unless otherwise indicated, when a Cartesian coordinate system is used, the width of an object is measured along the y-axis. Unless otherwise indicated, in the case of objects that would not be considered to have a uniform width, the width is measured at the widest part of the object. For example, for a solid object having an oblong cross-section, one would measure the width at the midpoint of the length of the object (i.e., where the object is the widest).

As used herein, the term "wound", in addition to having its ordinary meaning in the medical arts, can refer to any body part of a patient (such as a human or animal) that one may desire to subject to a course of treatment.

DETAILED DESCRIPTION OF CERTAIN EMBODIMENTS

The present disclosure is directed, among other things, to wound pads with features that facilitate shaping and sizing the wound pad into, for example, cavernous wounds of various shapes and sizes. In particular, in various embodiments, provided are wound pads whose thicknesses can be modified without the use of tools. Also provided are systems comprising such wound pads (for example, negative pressure wound treatment systems), kits comprising such wound pads, and methods of using inventive wound pads.

Wound pads of the present disclosure generally have a pad width, a pad length, and a pad thickness, with the pad thickness being less than the pad width and less than the pad length.

The disclosed wound pads 1 generally comprise a plurality of separable layers 20, 12, 22, each of which has a layer thickness that is less than the total thickness of the wound pad ("pad thickness"). For example, the separable layers can be separated from one another without the use of tools, e.g., only using human hands and without extraneous effort.

Each of the plurality of separable layers 20, 21, 22 comprises a first region 2 connected to at least one adjacent layer and a second region 10, 12 unconnected to any adjacent layer.

In some embodiments, the widths of each of the plurality of separable layers ("layer widths") within a given wound pad are substantially the same; in some such embodiments, the layer width of each of the plurality of separable layers is substantially the same as the total width of the pad ("pad width"). In other embodiments, the layer widths of the plurality of separable layers are not substantially the same; in other embodiments, the layer width of each of the plurality of separable layers is not the same as the pad width. In some embodiments, the lengths of each of the plurality of separable layers ("layer lengths") within a given wound pad are substantially the same; in some such embodiments, the layer length is substantially the same as the total length of the pad ("pad length"). In other embodiments, the layer lengths of the plurality of separable layers are not substantially the same; in other embodiments, the layer length of each of the plurality of separable layers is not the same as the pad length. In some wound pad embodiments, the layer widths are substantially the same and the layer lengths are substantially the same. For example, in some embodiments, the layer widths are substantially the same as the pad width and the layer lengths are substantially the same as the pad length.

Separable layers of the disclosed wound pads may be of any thickness that is smaller than the total thickness of the wound pad. Within a wound pad, layer thicknesses may each be substantially the same. Alternatively, at least one of the plurality of separable layers has a layer thickness that is different from a layer thickness of another one of the plurality of separable layers.

The number of separable layers in a given wound pad depends on the embodiment and may be at least two, at least three, at least four, at least five, or at least six or more. For example, in some exemplary embodiments, wound pads comprise two layers, each having a thickness of about 15 mm. As a further example, in some exemplary embodiments, wound pads comprise three layers, each having a thickness of about 10 mm. As a further example, in some exemplary embodiments, wound pads comprise three layers, including a middle layer having a thickness of about 15 mm and two additional layers, each having a thickness of about 7.5 mm.

By virtue of the first region in each of the plurality of separable layers, each layer is connected to at least one adjacent layer, and therefore the entire wound pad can be handled as a single piece. Nonetheless, the provision of the second region in each of the plurality of separable layers that is unconnected to any adjacent layer facilitates the separation of one layer from an adjacent layer without the use of tools. In some embodiments, each of the plurality of separable layers, when removed from the rest of the wound pad, can maintain its own structural integrity, i.e., it can be handled as a single piece itself. In some embodiments, removal of one or more of the plurality of separable layers modifies a single dimension of the overall wound pad without modifying the other overall dimensions. For example, removal of one of the plurality of separable layers can modify the pad thickness but does not modify the pad width or the pad length.

Figure 4A:
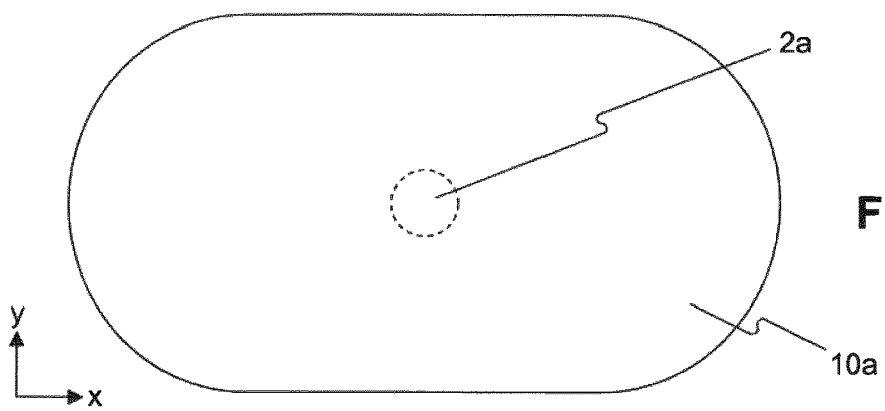
FIGS. 4A-4D depict top views of several exemplary wound pads.
Figure 4B:
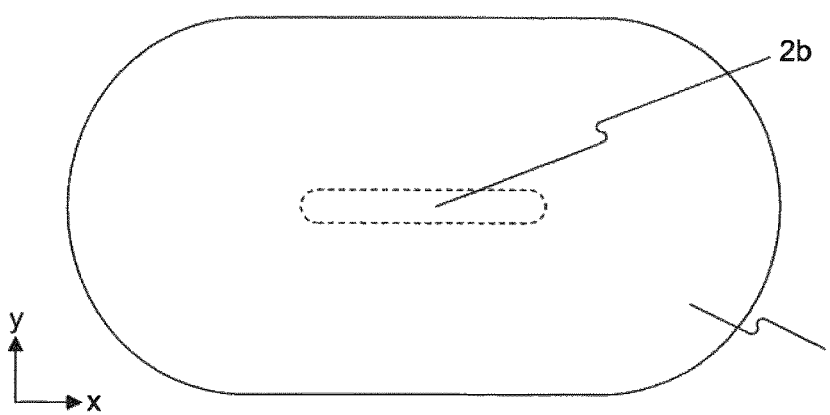
Figure 6A:
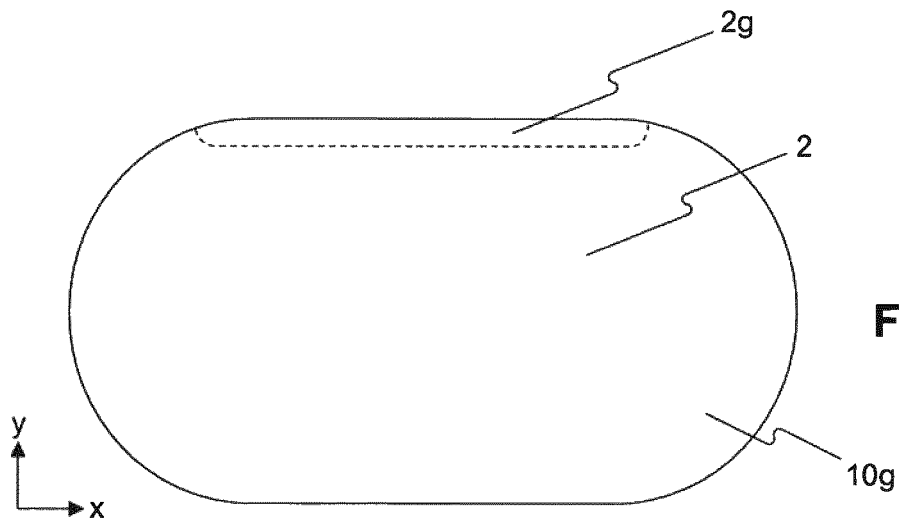
FIGS. 6A-C depict top views of exemplary wound pads, showing configurations in which a first region connected to at least one adjacent layer is disposed adjacent to a second region unconnected to any adjacent layer.
Figure 6B:
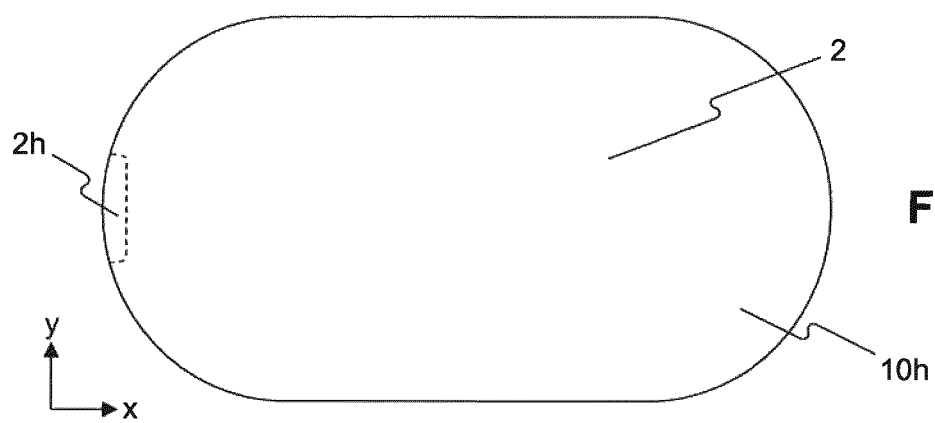
Figure 6C:
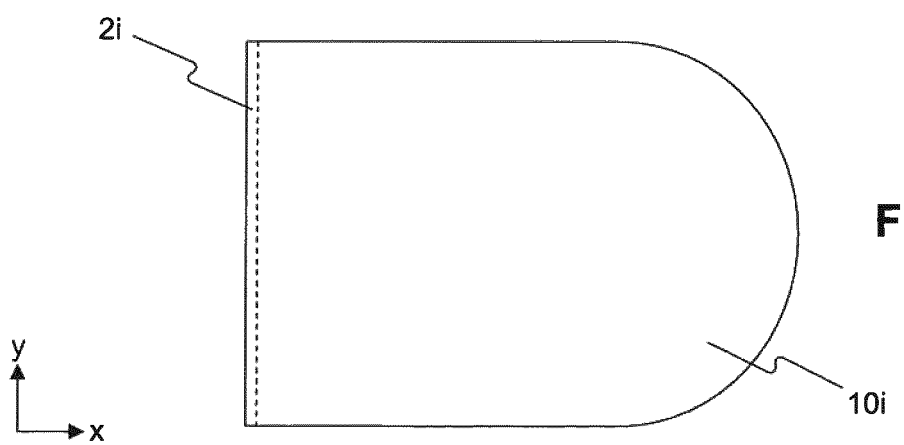

In some embodiments, the first region 2*a*, 2*b* is surrounded by the second region 10*a*, 10*b*. Non-limiting examples of such configurations are shown in FIGS. 4A and 4B. In some embodiments, the first region 2*g*, 2*h*, 2*i* is adjacent to the second region 10*g*, 10*h*, 10*i*. For example, the first region may be disposed at one edge of each of the plurality of layers. FIG. 6A shows an exemplary wound pad in which the first region 2*g* is disposed along the length of each of the plurality of separable layers. FIG. 6B shows an exemplary oblong-shaped wound pad in which the first region 2*h* is disposed along part of one edge. FIG. 6C shows an exemplary wound pad in which the first region 2*i* is disposed along the width of each of the plurality of layers.

In some embodiments, each of the plurality of layers includes a single connected region connecting it to an adjacent layer and a single unconnected region. That is, a given layer does not comprise any additional regions (i.e., either a region connected to at least one adjacent layer or a region that is unconnected to any adjacent layer). For example, a given layer may include a single connected region on a first side thereof connecting it to a first adjacent layer and a single connected region on a second side thereof, opposite the first side, connecting it to a second adjacent layer. That is, each side of the given layer may include only one connected region and/or only one unconnected region.

In some embodiments, each of the plurality of separable layers comprises additional regions. Any number of regions connected to at least one adjacent layer ("connected regions") is contemplated. Similarly, any number of regions unconnected to any adjacent layer ("unconnected regions") is contemplated. Within a single wound pad, connected regions of the plurality of layers may or may not be aligned with one another (i.e., lie at the same location in the x and y dimensions in each layer). For example, a given layer may include a first connected region at a first x-y coordinate location on a first side thereof and connecting the layer to a first adjacent layer and may further include a second connected region at a second x-y coordinate location on a second side of thereof, opposite the first side, and connecting the layer to a second adjacent layer. The first x-y coordinate location may be the same or different from the second x-y coordinate location. It is contemplated that the location and arrangement of connected regions for the plurality of layers may be the same and/or vary according to any pattern throughout the wound pad. Similarly, unconnected regions in the various layers may or may not align with one another.

Figure 5A:
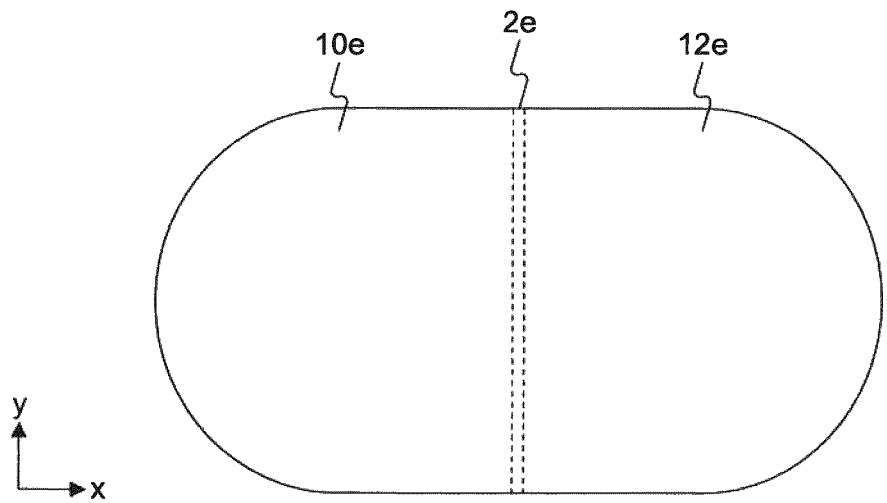
FIGS. 5A and 5C depict top views of exemplary wound pads, showing configurations in which a first region connected to at least one adjacent layer is disposed between a second and third region unconnected to any adjacent layer.
Figure 5C:
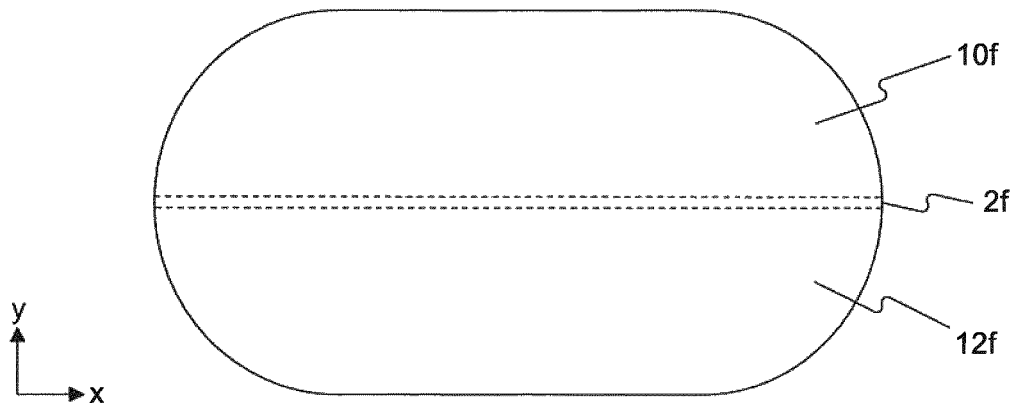

For example, in some embodiments, each of the plurality of separable layers further comprises a third region unconnected to any adjacent layer. In some such embodiments, within each of the plurality of separable layers, the first region 2*e*, 2*f* is disposed between the second 10*e*, 12*e* and third regions 10*f*, 12*f*. For example, in some embodiments, within each of the plurality of separable layers, the first region may be disposed within the middle third (lengthwise) of the wound pad, the middle third (widthwise) of the wound pad, or within the middle third both lengthwise and widthwise of the wound pad. For example, in some embodiments, within each of the plurality of separable layers, the first region may be disposed at the center lengthwise 2*e* and/or widthwise 2*f* of the wound pad. FIGS. 5A and 5C depict non-limiting examples of configurations of regions for such exemplary embodiments.

Figure 4C:
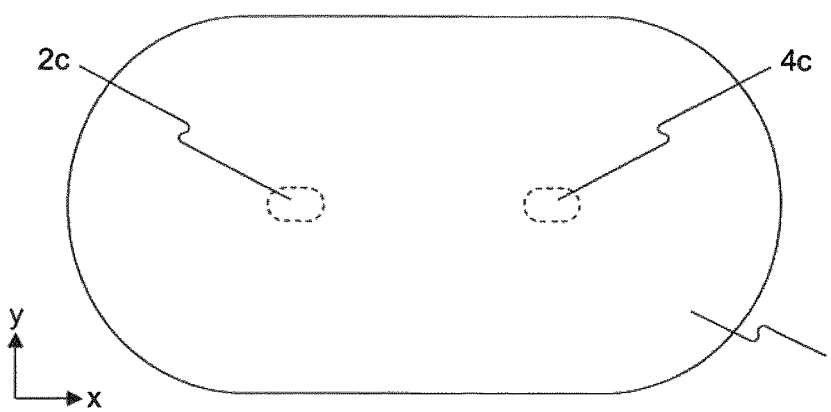
Figure 4D:
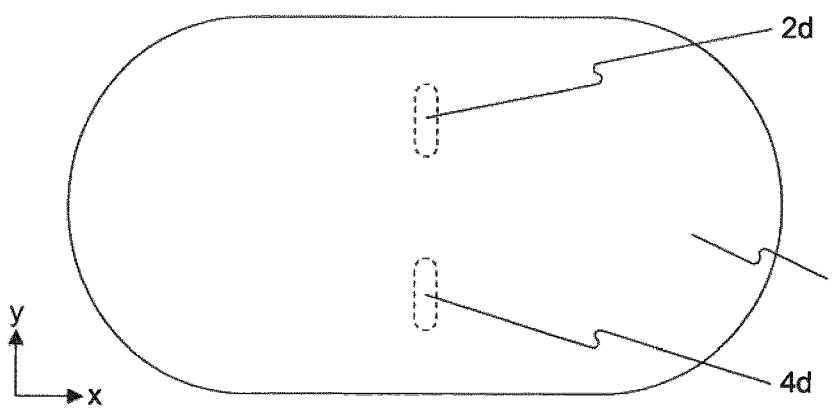

As another example, in some embodiments, each of the plurality of separable layers further comprises a third region connected to at least an adjacent layer. In some such embodiments, the first region 2*c*, 2*d* and third regions 4*c*, 4*d* are surrounded by the second region 10*c*, 10*d*. Non-limiting examples of such configurations are shown in FIGS. 4C and 4D.

The relative sizes and configurations of the regions of the each of the plurality of separable layers vary according to the embodiment.

In some embodiments, the ratio of the total areas of all connected regions in a given layer to the total area of all unconnected region in that layer is 1:5 or less. For example, the total area of connected regions may be about 15% or less, about 13% or less, about 10% or less, about 8% or less, about 5% or less, about 4% or less, about 3% or less, about 2% or less, or about 1% or less of the total area of unconnected regions.

A connected region can have any of a number of shapes. When there is more than one connection region in a given separable layer, the connected regions need not necessarily have the same shape. Examples of suitable shapes for connected regions include, but are not limited to, shapes that are or are substantially circles, ellipses, oblongs, and rectangular strips. In some embodiments, a connected region can be in the form of a dot or dash, and such a dot or dash may be a single dot or dash or part of a series of dots and/or dashes. It is contemplated that the series of dots and/or dashes may have any pattern of dots and/or dashes.

For example, in some embodiments, such as those depicted in FIGS. 5A and 5C, a connected region is in the shape of a rectangular strip or a substantially rectangular strip. In some embodiments, the rectangular strip has a length ("strip length") that is the same size as either the width or the length of the wound pad, and a width ("strip width") that is much smaller than the strip length. For example, the strip length can be the same size as the width of the wound pad, and the strip width is 20% or less of the strip length. In some embodiments, the strip width is 15% or less, 10% or less, 5% or less, 3% or less, 2% or less, or 1% or less of the strip length.

In some embodiments, the rectangular strip has a strip length that is less than the width of the wound pad, but more than a third the width of the wound pad, and a strip width that is much smaller than (e.g., 20% or less, 15% or less, 10% or less, 5% or less, 3% or less, 2% or less, or 1% or less of) the strip length.

In some embodiments, the relative sizes and configurations of the connected region(s) and unconnected region(s) in each separable layer is substantially the same for all of the separable layers of a given wound pad. In some embodiments, the relative sizes and configuration of the connected region(s) and unconnected region(s) of at least one separable layer is different from the relative sizes and configuration of the connected region(s) and unconnected region(s) in another one of the separable layers.

In some embodiments, provided are wound pads having a pad width, a pad length, and a pad thickness, wherein the pad thickness is less than the pad width and less than the pad length, that consist essentially of: a first separable layer, a second separable layer adjacent to the first separable layer on a first side of the second separable layer, and a third separable layer adjacent to the second separable layer on a side opposite to the first side of the second separable layer. In such embodiments, each separable layer has a layer thickness that is less than the pad thickness, a layer width that is substantially the same as the pad width, and a layer length that is substantially the same as the pad length. The first separable layer in such embodiments comprises a first region connected to the second separable layer, a second region unconnected to the second separable layer, and a third region unconnected to the second separable layer. The third separable layer in such embodiments comprises a first region connected to the second separable layer, a second region unconnected to the second separable layer, and a third region unconnected to the second separable layer. Furthermore, the first region of the first separable layer is disposed between the second and third regions of the first separable layer; and the first region of the third separable layer is disposed between the second and third regions of the third separable layer.

In some embodiments, a single piece of material is cut into the shape of the wound pad, and the material is further cut to form one or more unconnected regions in each layer. For example, in some embodiments, a series of substantially parallel cuts are made into a wound pad-shaped material, each cut made in a plane substantially parallel to that defined by the length and width dimensions of the wound pad-shaped material. Each cut does not extend all the way through the wound pad, so as to leave one or more connected regions in the separable layers. Therefore, in some embodiments, the plurality of separable layers in a given wound pad is both homogeneous and consanguineous. In some embodiments all of the cuts made in the wound pad are substantially parallel to one face (e.g., an outer surface) of the wound pad. For example, all of the cuts are oriented in substantially the same direction, at the same orientation, and along the same axis of the wound pad.

Figure 2:
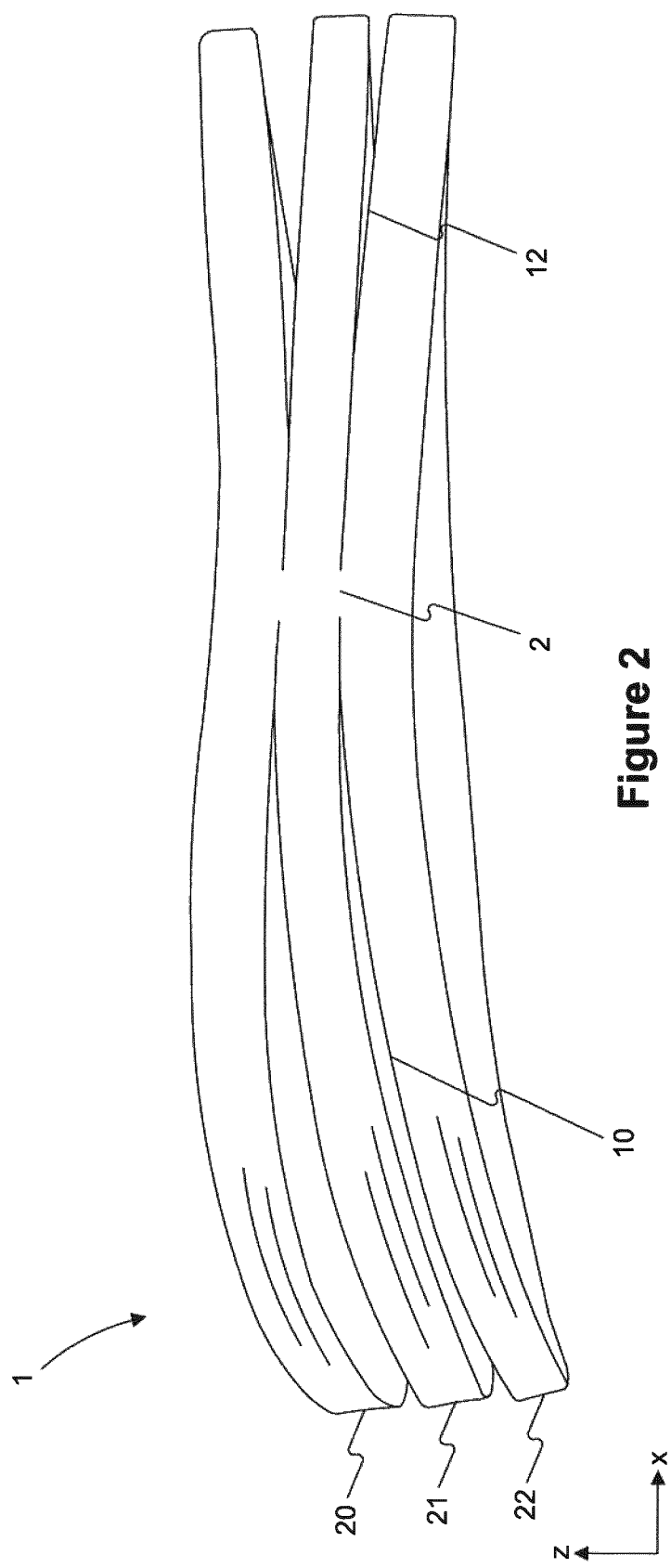
FIG. 2 depicts a side view of an exemplary wound pad having three separable layers.
Figure 7A:
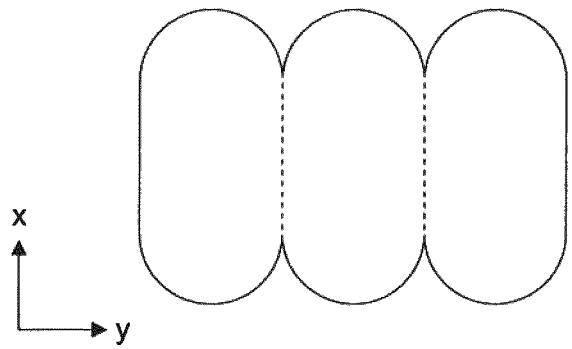
FIGS. 7A-C illustrates how some exemplary wound pads can be made.
Figure 7B:
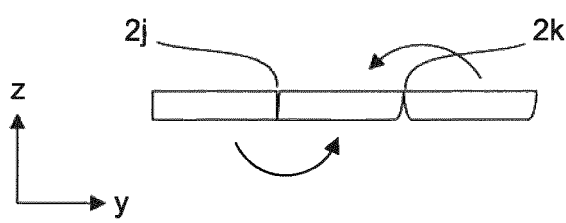
Figure 7C:
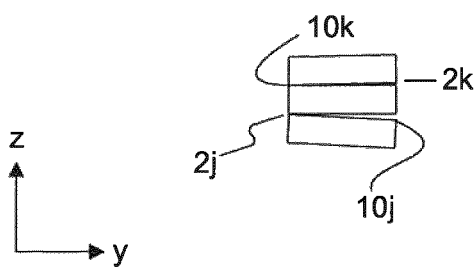

As a further example, in some embodiments, a single piece of material is cut such that multiple similarly sized and shaped sections can be folded on top of one another to form a wound pad having a plurality of separable layers. For example, a single piece of material can be cut as shown in FIG. 7A, with the area between any two adjacent sections (marked by dotted lines) being incompletely cut through the thickness to leave connected regions between adjacent sections. In some embodiments, the connected regions are disposed on the same side within the thickness, i.e., near the top or bottom surface of the material. Such an embodiment is shown in a top-view in FIG. 7A. In some embodiments, the side within the thickness on which the connected region is disposed alternates, e.g., as shown in FIG. 7B, 2$j$, 2$k$ such that the sections can be folded on top of another to form a wound pad comprised of separable layers, each layer having substantially the same thickness. FIG. 7C depicts a side view of an exemplary wound pad that can be folded in such a manner, having three separable layers, each of which has a connected region 2$j$, 2$k$ with at least one adjacent layer and a region unconnected 2$k$, 10$j$ with at least one adjacent layer.

It will be understood by one of ordinary skill in the art that any of a number of techniques can be used to cut the pad, including, but not limited to, blade cutting, die cutting, wire cutting, water jet cutting, laser cutting, and combinations thereof.

In some embodiments, the disclosed wound pads are made by laminating together several individual layers of thinner wound pads at one or more regions within the wound pad connection region(s)). Lamination can be performed any of a number of techniques, such as, but not limited to, stitching or sewing, an adhesive, heat, a laser, ultrasonic welding, and combinations thereof. Those of ordinary skill in the art will be able to choose the appropriate lamination technique(s), considering, for example, the type of material, the dimensions of the layers to be connected together, and the configuration, size, and shape of any desired connected regions. In some embodiments, lamination is performed by ultrasonic welding to form one or more connection region(s). Such a process can be streamlined and may be less costly than other available methods.

In some embodiments, the individual layers of thinner wound pads that are laminated together are made of the same material; consequently, the wound pad is homogeneous throughout.

In some embodiments, the individual layers of thinner wound pads that are laminated together are made of materials that differ in at least one aspect. For example, the individual layers may be made of materials having the same chemical composition, but different pore sizes. In particular, some contemplated wound pads comprise 1) one or more individual layer(s) having smaller pore sizes (relative to pore sizes in the other layers) intended to be applied adjacent to or close to a wound bed and 2) one or more additional individual layer(s) having larger (i.e., more open) pore sizes. Such a configuration may reduce or prevent tissue ingrowth into the wound pad.

In some embodiments, a cutting technique is used to create one or more unconnected regions, but leaving one or more connected regions by not cutting through the material completely, and a lamination technique is further used to create one or more additional connected regions.

Any of a number of suitable materials can be used in the practice of the disclosed wound pads.

Features of the present disclosure are particularly suitable for wound pads made of less conformable (e.g., at least semi-rigid) materials that are difficult to fit into a wound without modifying the size and/or shape of the wound pad.

For example, some exemplary wound pads may comprise a foam, for example, a semi-rigid foam.

In some embodiments of the present disclosure, exemplary wound pads comprise a porous foam. The porous foam may be, for example, an open-cell foam. Alternatively or additionally, exemplary wound pads may comprise a closed-cell foam that comprises through-holes. The through-holes may extend through the entirety of one dimension (e.g., the thickness) of the wound pad. Such embodiments may allow fluid to flow through the wound pad, and may be particularly suited for use in negative pressure wound treatment systems as described hereinbelow. Porous foams may be made of any suitable material, including, but not limited to, polymer foams as described herein.

In some embodiments of the present disclosure, exemplary wound pads comprise a polymer foam, which may or may not be porous. Non-limiting examples of suitable polymer foams include polyurethane foams, polyvinyl alcohol foams, silicone foams, polyolefin foams, alginate foams, and combinations thereof. In some embodiments, the polymer foam comprises a polyurethane foam. Non-limiting examples of suitable polyurethane foams include polyester-based and polyether-based foams.

In some embodiments of the present disclosure, exemplary wound pads are hydrophobic. As a non-limiting example, AVANCE™ Foam sold by Mölnlycke Health Care is made of a hydrophobic reticulated polyurethane foam with a large open cell structure. Such a material is also suitable for making wound pads of the present disclosure.

In some embodiments of the present disclosure, exemplary wound pads are hydrophilic or treated with an agent that makes the foam hydrophilic.

Generally, the wound pads of the present disclosure are suitable for use as a wound filler and, are thus, generally biocompatible or treated such that they are biocompatible. Furthermore, in some embodiments of the present disclosure, exemplary wound pads are sterilized, and/or biodegradable, hypoallergenic, or both.

Wound pads of the present disclosure may be made in any suitable size. Contemplated embodiments include, but are not limited to, pads that are 1) substantially planar and oblong or 2) substantially planar and substantially rectangular in shape. For example, substantially planar wound pads have a thickness, a width, and a length, and the thickness is substantially constant and significantly smaller than the overall pad's width and significantly smaller than the overall pad's length. For example, the pad's thickness may be 50% or less of the smaller of the pad's width and the pad's length. In some embodiments, the pad's thickness is 40% or less, 35% or less, 30% or less, 25% or less, 20% or less, 15% or less, 10% or less. Substantially rectangular wound pads have a shape that is nearly that of a rectangle, but with, for example, rounded corners. For shapes that would not be considered to have a constant length and/or width, such as oblong shapes, the length is measured at the longest part of the object and/or the width is measured at the widest part of the object, as appropriate.

In exemplary embodiments, suitable dimensions of wound pads that are substantially planar include, but are not limited to a length of at least 10 cm, a width of at least 8 cm, and a thickness of between about 0.75 cm and 3 cm. For example, some exemplary wound pads are about 10 cm length by about 8 cm width by about 3 cm thickness; some are about 20 cm length by about 12 cm width by about 3 cm thickness; and some are about 26 cm length by about 15 cm width by about 3 cm thickness.

In some embodiments, for example, when the disclosed wound pads are intended to be used for particularly large wounds (such as, for example, open abdominal wounds), the dimensions are much larger. For example, suitable dimensions of wound pads that are substantially planar and intended for large wounds include, but are not limited to a length and a width each of at least about 25 cm and a thickness of between about 0.75 cm and about 3 cm (such as, for example, about 0.75 cm, about 1 cm, about 1.5 cm, about 2 cm, about 2.5 cm, or 3 cm). In some embodiments, the thickness of wound pad is about 1 cm or about 1.5 cm. As a non-limiting example, some inventive wound pads are approximately 45 cm length by 30 cm width by 1.5 cm thickness or 45 cm length by 30 cm width by 2 cm thickness.

Some exemplarily disclosed wound pads may include one or more further features that also allow a user to modify the length and/or width of the wound pad without the use of tools. Thus, in some embodiments, a user can not only modify the thickness (by pulling apart one or more separable layers), but can also modify the length and/or width (by pulling apart sections of the wound pad defined by one or more additional cuts as described herein), all without the use of tools.

For example, in some embodiments of the present disclosure, exemplary wound pads further comprise at least one cut that extends throughout the entire thickness of the wound pad. The cut can delineate, either by itself or in combination with at least one other cut, a portion of the wound pad that can be removed without the use of tools.

In some embodiments, the wound pads may further comprise a plurality of cuts extending through the entire pad thickness, that is, a series of cuts. In some such embodiments, each of the plurality of cuts forms, together with at least one other cut, a part of a closed shape (for example, a substantially curvilinear closed shape); and a connected region is disposed between any two adjacent cuts. For example, the plurality of cuts and connected regions may form a series of alternating cuts and connected regions, i.e., perforations, in any suitable pattern. In some embodiments, the plurality of cuts combined form at least two concentric closed shapes. Examples of suitable closed shapes include, but are not limited to, substantially curvilinear closed shapes such as oblongs, ellipses, and circles.

Figure 8:
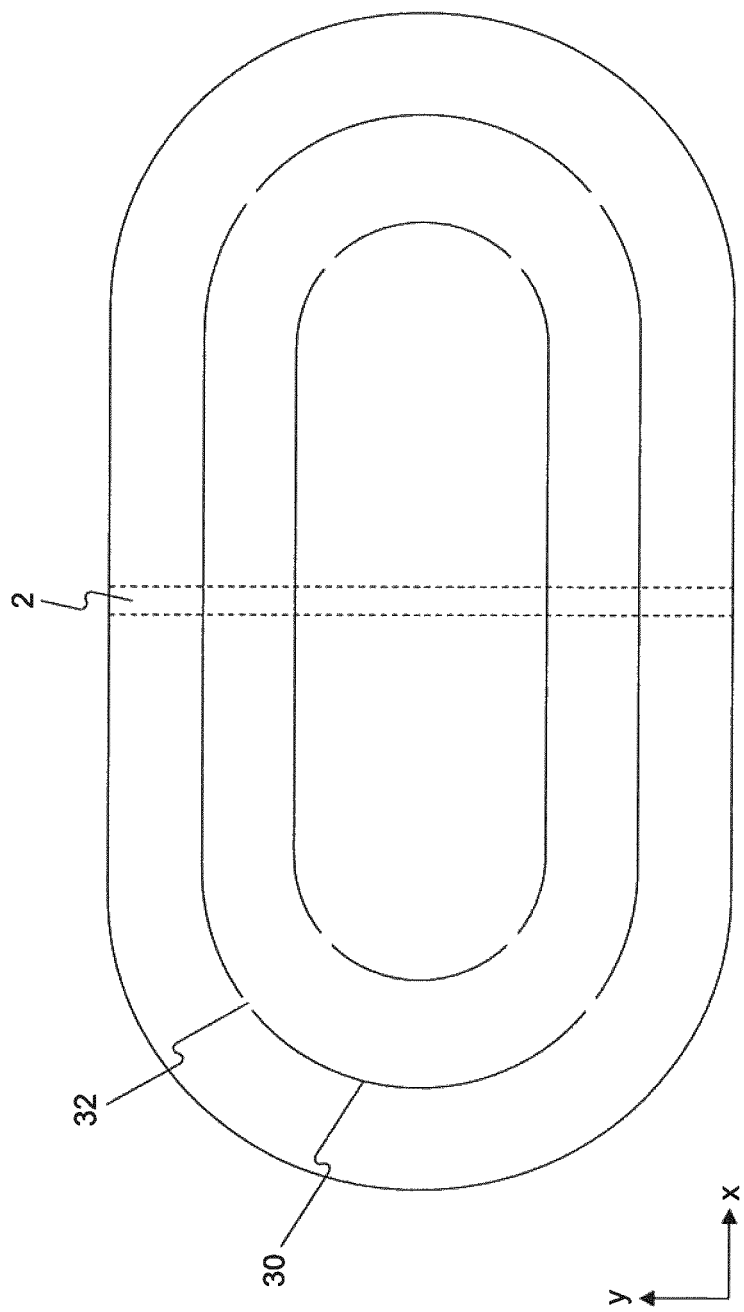
FIG. 8 depicts a top view of an exemplary wound pad that, in addition to having at least two separable layers (not visible in this view), also has a pattern of perforations extending through the entire thickness of the wound pad. The cuts form two concentric oblong shapes, each oblong shape being comprised of a plurality of cuts and uncut regions disposed between adjacent cuts.

As just one example, FIG. 8 depicts the top view of an exemplary wound pad that has a series of additional cuts and inter-disposed connected regions, that form a pattern of two concentric oblong shapes 30, 32. The oblong shapes include a plurality of cuts extending through the entire pad thickness, as well as a plurality of connected regions disposed between adjacent cuts.

Similar to connected regions of separable layers as previously described, connected regions that are disposed between adjacent cuts can result from regions that have not been cut at all, and/or by laminating together two sections of the wound pad that had been previously cut.

In certain embodiments of the present disclosure, the wound pads and kit components are sterilized so that they are medically acceptable, e.g., appropriate for use in wound care. Sterilization can be achieved by any one or a combination of known protocols in the art, some of which are standardized and/or approved by regulatory bodies. Non-limiting examples of sterilization methods for wound care products include autoclaving, exposure to dry heat, exposure to ultraviolet radiation, ethylene oxide treatment, gamma irradiation, immersion in aqueous alcohol solutions (e.g., 70% or greater concentrations of ethanol), gas plasma technology, steam sterilization, and electron beam irradiation. The choice of sterilization method can be influenced by a factor such as the type of material, which may have varying abilities to withstand and/or retain desirable characteristics under different sterilization protocols. For example, some ethylene oxide treatment protocols are well-suited for sterilization of polymer foam materials.

In another aspect of the present disclosure is directed to systems for negative pressure wound treatment that comprise a negative pressure source for providing negative pressure to a wound, a wound cover, a conduit configured to transmit negative pressure from the negative pressure source to the wound, and an exemplary wound pad as described herein that is suitable for use as a wound filler.

In use, the wound cover is disposed over the wound with the wound pad in the wound. The conduit is fluidly coupled at one end (hereinafter the "proximal end") to the wound and at one end (hereinafter the "distal end") to the negative pressure source. In some embodiments, the proximal end of the conduit is placed into the wound underneath the wound cover. In some embodiments, the proximal end of the conduit is placed above the wound cover and fluidly connected to the wound cavity via a hole or port in the wound cover. The wound cover can be supplied with a hole or port, and/or a hole or port can be created for such a purpose.

In some embodiments of the present disclosure, the systems further comprise any or a combination of: one or more wound contact layers disposed inside the wound beneath the wound pad, a wound interface device between the conduit and the wound cover, and/or a storage canister in fluid communication with the conduit for collecting fluid such as wound exudate. In embodiments comprising a storage container, a filter may be included to prevent fluids, aerosols, and/or other contaminants from leaving the container.

Figure 9:
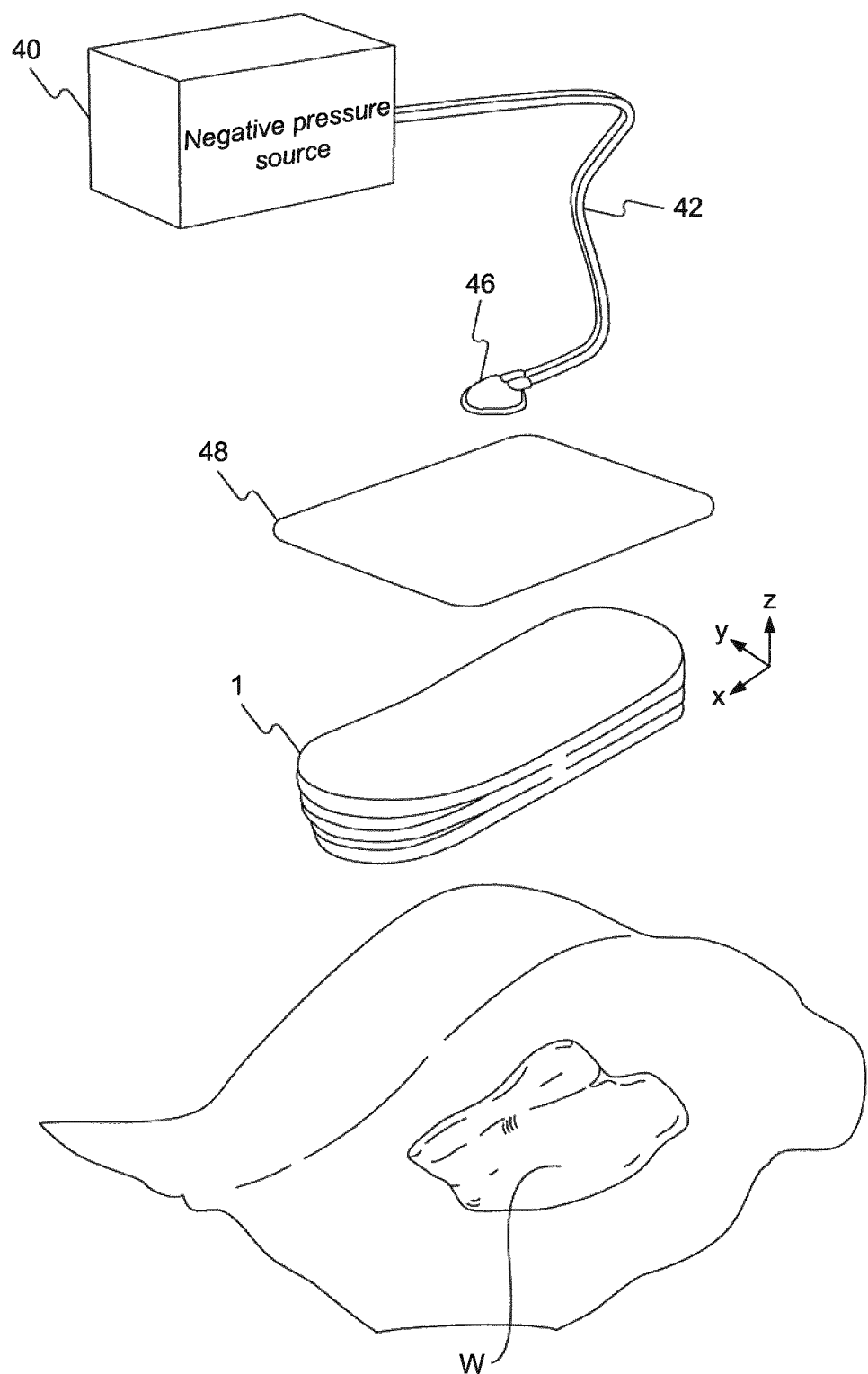
FIG. 9 depicts an exemplary negative pressure wound treatment system.

An exemplary embodiment of a system for negative pressure wound treatment is illustrated in FIG. 9. The system comprises a negative pressure source 40 for providing negative pressure to a wound W, a wound pad 1 of the present disclosure as described herein is configured to be placed into the wound W. The system also includes a wound cover 48. A conduit 42 is configured to transmit negative pressure from the negative pressure source 40 to a connector 46 and thus to the wound W for treatment. The would cover 48 is configured to substantially the wound W and includes an opening substantially sealingly connected to the connector 46. In FIG. 9, the illustrated conduit is a multi-lumen conduit with a parallel lumen configuration; however, as explained below, a single lumen and/or other multi-lumen configurations may be used. An optional interface device may be included, although contemplated embodiments include those without interface devices.

The negative pressure source may comprise a pump, non-limiting examples of which include vacuum pumps (e.g., electrically-driven vacuum pumps, manually actuated pumps, piezoelectric-actuated pumps, etc.), circulation pumps, dual action vacuum/pressure pumps (e.g. for drainage and irrigation), peristaltic pumps, syringe pumps, bellows pumps, diaphragm pumps, and combinations thereof. Pumps in systems of the present disclosure are generally adapted to provide a negative pressure value that is suitable for treatment protocols standard in the art. In some embodiments, the negative pressure source includes one or more pressure sensors for detecting a pressure within the system.

Depending on the embodiment, the negative pressure source may be adapted to provide negative pressure at a fixed negative pressure value or may be adapted to provide negative pressure at one of multiple values which may be selected, for example, by the user and/or depending on the therapy mode. In some embodiments, the negative pressure source is adapted to provide negative pressure at various values within a range. In some such embodiments, the negative pressure source is adapted to provide negative pressure at any value in certain increments from a lower limit (absolute value) to an upper limit (absolute value).

The negative pressure source may be adapted to provide negative pressure continuously during treatment. Alternative or additionally, the negative pressure source is adapted to provide negative pressure intermittently during treatment.

Generally, the negative pressure source is adapted to provide negative pressure at one or more values that fall within the range between about 20 mm Hg and about 400 mm Hg (inclusive of endpoints; values herein refer to the absolute values of negative pressure unless otherwise indicated).

It is contemplated that the threshold values used during negative pressure wound therapy may include, for example, any value in the range between about 20 mm Hg and about 400 mm Hg (inclusive of both endpoints), for example, about 20 mm Hg, about 25 mm Hg, about 50 mm Hg, about 60 mm Hg, about 80 mm Hg, about 120 mm Hg, about 200 mm Hg, or about 300 mm Hg. For example, in some embodiments, a negative pressure of about 80 mm Hg is used. In some embodiments, a negative pressure of about 120 mm Hg is used. In some embodiments, a negative pressure of about 80 mm Hg is used. In some embodiments, a negative pressure of about 40 mm Hg is used.

The selection of the appropriate values may be made, for example, by a clinician or patient. The choice of appropriate negative pressure value(s) may be influenced by any or a combination of factors such as location of wound, type of wound, wound healing status, type and/or material of wound pad, type of dressing, patient, etc. In some embodiments where the wound pad is comprised of a polymer foam, a negative pressure of about 120 mmHg is used.

In some embodiments, the negative pressure source may be adapted to provide a negative pressure, the absolute value of which is greater than or equal to about 120 mmHg or about 180 mmHg.

Any of a variety of wound covers compatible with negative pressure wound treatment systems can be used. Generally, the wound cover is adapted to be attached to the skin surrounding the wound, and, either alone or in combination with one or more other components of the negative pressure system, forms an airtight seal over the wound. Non-limiting examples of suitable wound covers include plastic films, e.g. polyurethane films.

The wound cover can be attached to the skin surrounding the wound, for example, by means of an adhesive. Wound covers may comprise an adhesive, and/or be used with an adhesive that is applied before use. Examples of adhesives that may be used include, but are not limited to, acrylic adhesives and/or silicone gel adhesives. In some embodiments, the adhesive or adhesives is/are already incorporated as part of the wound cover. In some embodiments, the adhesive or adhesives is/are applied to the wound cover member during use.

For example, a suitable wound cover is AVANCE™ Transparent Film sold by Mölnlycke Health Care AB, which is a polyurethane film with an acrylic adhesive. Also suitable for use in embodiments of the present disclosure is AVANCE™ Film with SAFETAC™ technology (also sold by Mölnlycke Health Care AB), which comprises a layer of perforated polyurethane coated on one side with silicone gel. As a non-limiting example, the adhesive sold under the trademark MEPISEAL™ by Mölnlycke Healthcare AB may be used for attaching the wound cover member to the skin surrounding the wound.

In some embodiments, the conduit is provided via a single lumen tube. In some embodiments, the conduit is provided as part or all of a multi-lumen tube, for example, wherein one lumen is used to provide negative pressure to the wound, and one or more additional lumens may be used for another purpose, e.g., circulation, measurement (e.g. of pressure), irrigation, etc. In embodiments with multiple lumens, any of a variety of possible arrangements of the lumens is possible, e.g., parallel lumen arrangements, central and peripheral lumen arrangements, etc.

In some embodiments, fluid is transported via the conduit. For example, wound exudates may be transported away from the wound via the conduit. In embodiments with a canister, wound exudates may be transported into the canister.

In some embodiments, the negative pressure wound treatment systems also comprise one or more wound contact layers disposed inside the wound beneath the wound pad. Such wound contact layers are generally made of a biocompatible material and, may, for example, help prevent sticking of the wound to the wound pad. For example, one suitable wound contact layer is the MEPITEL™ dressing sold by Mölnlycke Health Care AB, which is a perforated polyamide fiber elastic material coated on both sides with a tacky soft silicone gel. As a further example, the MEPITEL™ One dressing (also sold by Mölnlycke Health Care AB) is a perforated polyurethane sheet coated on one side (which side can be used as the wound-contacting side) with a tacky silicone gel.

In some embodiments, the negative wound treatment systems comprise a wound interface device (a device that provides an interface between the conduit and the wound cover). Such wound interface devices are adapted to allow sealed passage of fluid (e.g. gas and/or liquid) between the wound and the conduit. In some embodiments, a hole or port through the wound cover is created and/or provided by the interface device to allow flow of fluid out of and/or into the wound to the conduit. Non-limiting examples of wound interface devices suitable for such purposes and known in the art include the AVANCE™ Transfer Pad sold by Mölnlycke Health Care AB as part of a kit for negative pressure wound treatment.

In some embodiments, a canister is provided and arranged so as to allow collection of fluid from the wound (e.g., wound exudates) via the conduit. For example, the conduit may be provided in two parts, one connecting the wound to the canister, and the other connecting the canister to the negative pressure source. Thus, while negative pressure is transmitted from the negative pressure source to the wound via the conduit, fluid may also be drawn from the wound and collected into a canister.

In another aspect, the present disclosure is directed to kits for use in negative pressure wound treatment. Such kits generally comprise at least one wound pad as described herein substantially sealed within an interior of a package that surrounds the wound pad.

In some embodiments, the kits may also include one or more items selected from the group consisting of: a wound contact layer as described herein, a wound cover as described herein, and a device that provides an interface between a wound ("wound interface device", as described herein), and a conduit. The one or more items may or may not be substantially sealed within the interior of the package that surrounds the wound pad. For example, in some embodiments, the kits include a wound pad as disclosed herein, a wound cover, and a wound interface device, all substantially sealed within an interior of a single package. In some embodiments, the kits include a wound pad as disclosed herein and a wound cover, both substantially sealed within an interior of a single package. In some embodiments, the kits include a wound pad as disclosed herein and a wound interface device, both substantially sealed within an interior of a single package.

Generally, the present disclosure, and in particular the disclosed wound pads, may be used with any cavity wound, whether chronic or traumatic, in any medical context where it is desirable to fill the wound, for example, during at least part of a course of treatment. Non-limiting types of cavity wounds include open wounds, pressure ulcers ("pressure sores"), diabetic ulcers, and burns. Open wounds include both surgically created and non-surgically created wounds. For example, open wounds in the abdominal or peritoneal cavity can be filled using the disclosed wound pads.

It is contemplated that the disclosed wound pads, systems, and kits of the present disclosure may be used for wounds in any part of the body. In some embodiments, inventive wound pads, systems, and/or kits, are used during the course of negative pressure wound treatment, during which negative pressure is applied to a wound to facilitate healing of a wound and/or closure of a wound.

In another aspect of the present disclosure, the wound pads may be fitted and placed into a cavity wound using, for example any of the inventive methods described below. These methods for modifying the size or shape of a wound pad generally comprise steps of (a) determining that the wound pad is too thick for a cavity wound to be treated, wherein the wound pad has a pad thickness, and comprises a plurality of separable layers, each layer including: a layer thickness that is less than the pad thickness, a first region connected to at least one adjacent layer, and a second region unconnected from any adjacent layer; (b) removing at least one of the plurality of separable layers without the use of tools to obtain a modified wound pad and one or more separated layers; and (c) inserting either the modified wound pad or the at least one separated layers into the cavity wound.

The methods may also include a step of providing a wound pad. Any wound pad of the present disclosure as described herein can be modified according to methods described herein, and/or provided in the step of providing.

To determine that the provided wound pad is too thick for the cavity wound, a clinician or other user may inspect the wound visually with or without the use of tools, for example, to lift up folds of flesh. The clinician or other user may or may not use a measuring tool to measure one or more dimensions of the wound cavity.

To remove at least one of the separable layers of the wound pad, the clinician or other user may grasp the layers to be separated with one hand and the remainder of the wound pad with another hand, pulling the two parts of the wound pad apart to disrupt any connection (e.g., at one or more connection regions between one layer and the layer adjacent to it). The user may therefore obtain, without the use of tools, a modified wound pad and at least one separated layer, both of which are thinner than the original provided pad, and either of which may be used to fill the wound cavity.

It is contemplated that a user may opt to use tools (such as scissors) to further modify the shape and/or size of the wound pad. However, even in such cases, provided methods may be advantageous. Tools used by the end user tend to be cumbersome to use in that they typically provide less precision cutting, and/or generate debris from the material being cut. Thus, reducing the use of tools, even in cases where the use of tools cannot be completely eliminated, can be advantageous.

EXAMPLES

The following examples describe some of the modes of making and practicing the present disclosure. However, it should be understood that these examples are for illustrative purposes only and are not meant to limit the scope of the present disclosure. Furthermore, unless the description in an Example is presented in the past tense, the text, like the rest of the specification, is not intended to suggest that experiments were actually performed or data were actually obtained.

Example 1—Wound Pads

Wound pads having a generally oblong shape (similar to those embodiments depicted in FIGS. 1-3) were blade cut from a block of a hydrophobic reticulated polyester-based polyurethane foam material. The wound pads had approximate overall dimensions of 26 cm length by 15 cm width by 30 mm total thickness. (Length and width measurements were taken at the midpoint width-wise and length-wise; thickness was constant throughout the wound pad).

Using blade-cutting, each homogeneous wound pad was partially cut into three thinner layers (that is, each was cut along two planes that are both parallel to x-y plane depicted in FIGS. 1 and 2) such that each wound pad was substantially divided into three layers having substantially the same thicknesses of about 10 mm each. Each of the three layers within a wound pad had the same oblong shape and same size in the x- and y-dimensions (length and width dimensions, as shown in FIGS. 1 and 2).

Figure 3:
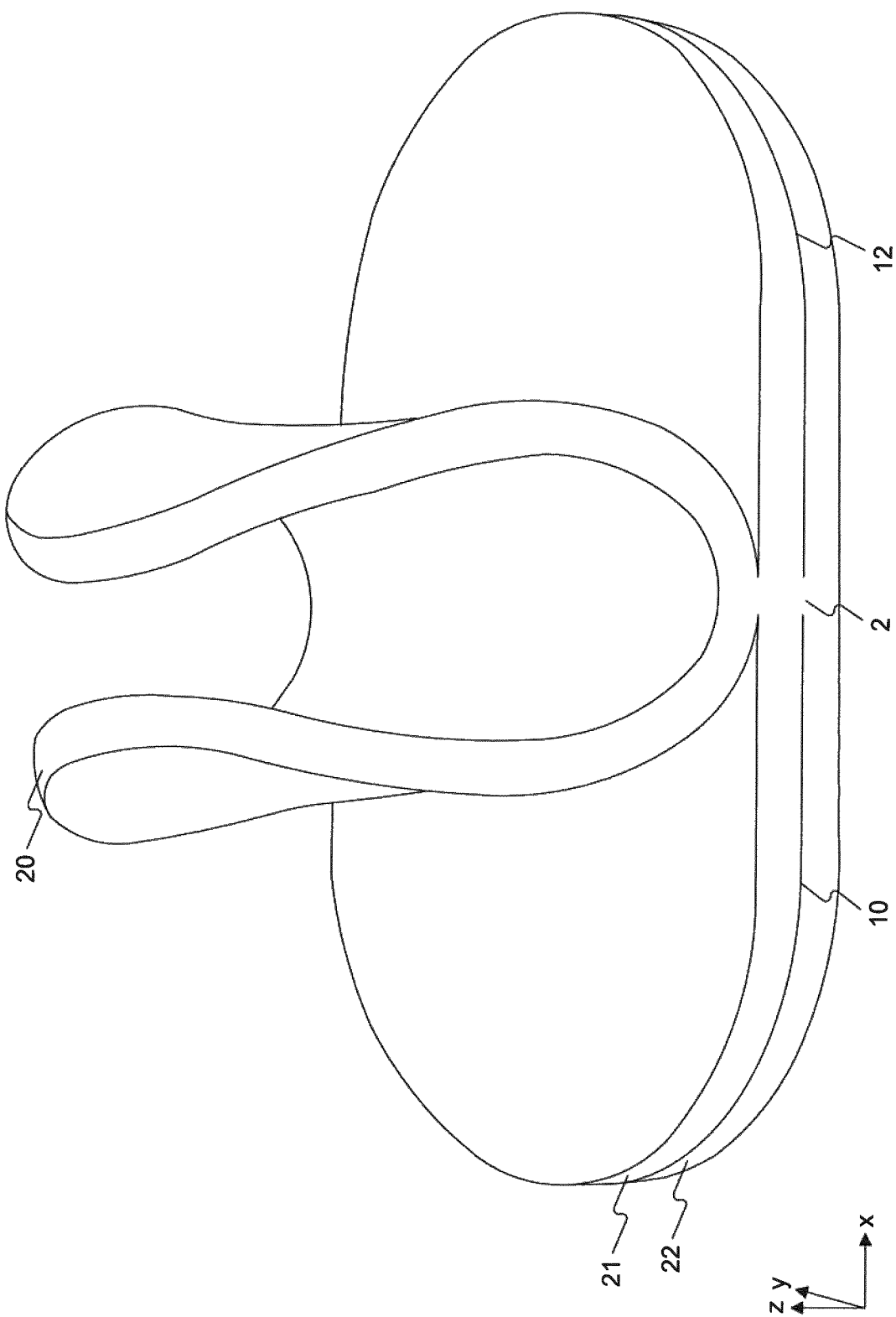
FIG. 3 depicts a perspective of an exemplary wound pad having three separable layers, with the top layer being lifted up at unconnected regions.

As shown in FIG. 3, which depicts a wound pad in which one of the layers is lifted up from the other layers, cuts extended from each end of the wound pad toward the center of the length dimension of the wound pad, but did not extend completely through the midpoint (length-wise) of the wound pad. Thus, each layer of the wound pad was still connected to at least one other layer, and the entire wound pad could be handled as a single piece. However, each layer could also be separated from the others to yield, e.g., 1) a wound pad having 20 mm thickness and a wound pad having 10 mm thickness or 2) 3 wound pads each having 10 mm thickness.

The sizes of the areas in which one layer was still connected to an adjacent layer (e.g. "connection region") varied according to the wound pad, but generally ranged from a strip of about 1 mm to about 5 mm along the length dimension that extended throughout the entire width of the wound pad (e.g., 15 cm).

To test the ability of the layers in the wound pad to be separated manually (e.g., without the use of tools), the layers were pulled apart by hand. All wound pads (no matter the size of the connection regions) were easily pulled apart into separate layers without compromising the integrity of the material within each layer.

The foam material from which the wound pads were made is biocompatible and has a large open cell structure. Properties of the foam material were previously measured on samples having the same material composition, and obtained by the same supplier, as the material that was used to make the prototypic wound pads. Samples used for tests were 30 mm in thickness. The material had a cell number of about 7 cells per centimeter, a density of about 30 kg/m$^3$, a dry tensile strength of about 165 kPa, and a wet tensile strength of about 125 kPa. Dry tensile strength was measured by the ISO 1798:1997 standard with the following deviation: the material thickness used in the test was increased to 30 mm. Wet tensile strength was measured on foam material that had been submersed in a Solution A (described herein) for 80 hours, then subjected to the test conditions described for dry tensile strength (e.g., using the ISO 1798:1997 standard with the above-noted deviation). A suitable Solution A can be prepared for example, as follows: for one liter of Solution A, dissolve about 8.298 g of sodium chloride (NaCl) and 0.368 g of calcium chloride dehydrate (CaCl$_2$.2H2O) in deionized water and fill up to 1 liter in a volumetric flask.

Example 2—Wound Pads

Wound pads having a generally oblong shape are cut from a homogeneous block of a hydrophobic reticulated polyester-based polyurethane foam as described in Example 1. The wound pads are partially cut into three thinner layers (as described in Example 1) by blade cutting, with the center (length-wise) remaining uncut, such that each wound pad is nearly divided into three layers having substantially the same thicknesses of about 10 mm each.

In addition, the wound pads comprise a pattern of cuts (depicted in FIG. 6, which shows a top view of the x-y plane) that extend through the entire thickness of the wound pad. Each cut is part of an approximately oblong shape that is concentric to other oblong shapes that comprise cuts. The cuts are made by blade cutting, and certain portions within each oblong shape of cuts are not cut, such that each oblong shape of cuts has portions where the wound pad is not cut through the thickness of the wound pad (in FIG. 6; "connection regions"). Thus, the wound pad can be handled as a single piece, though the pattern of cuts in the x-y plane allow the wound pad's size in the x-y dimensions (e.g., length and width) to be modified manually, e.g., without the use of tools, by a user, while at the same time the cuts forming the plurality of layers allow the wound pad's thickness in the z dimension to be modified manually, e.g., without the use of tools, by a user.

Example 3—Use as a Wound Filler

A cavity wound is cleaned with 0.9% saline. The healthy skin surrounding the wound is dried. Optionally, a protective cream or ointment is applied to the healthy skin. The wound is kept moist.

The size and shape of the cavity wound is inspected. A wound pad of the present disclosure, such as those described in Example 1 or 2, is optionally re-sized so as to fit the wound by manually pulling away layers of the wound pad delineated by partial cuts (so as to modify the thickness of the wound pad) and/or portions of the wound pad delineated by cuts that form an oblong pattern (so as to modify the length and width of the wound pad).

It is contemplated that further trimming, e.g., with scissors and/or a scalpel, may be used if needed. The wound with the wound pad inside it is covered with a secondary dressing that is appropriately chosen for the exudate level of the wound.

Example 4—Use as a Wound Filler During Negative Pressure Wound Treatment

A wound pad as described in Example 1 or 2 is used to fill a wound cavity as described in Example 3, except that no secondary dressing is used, and no protective cream or ointment is used. Optionally, an agent that enhances adhesiveness is applied to the skin. A wound cover is placed over the wound cavity (with the wound pad inside it), extending over the edges of the wound and forming a seal with the skin on the edges of the wound. A hole is then cut in the wound cover, and the conduit with the wound interface device is arranged with the hole aligned so that negative pressure can be transmitted from the negative pressure source to the wound. The conduit is connected to a negative pressure source, which is then switched on.

We claim:

1. A wound pad, having a pad width, a pad length, and a pad thickness, wherein the pad thickness is less than the pad width and less than the pad length, comprising:
    a plurality of separable layers configured to be removed from each other, each layer having:
        a layer thickness that is less than the pad thickness,
        a first region connected to at least one adjacent layer, and
        a second region unconnected from any adjacent layer,
    wherein removal of a single one of the plurality of separable layers from the remainder of the plurality of separable layers reduces the pad thickness, and
    wherein the plurality of separable layers are constructed from a single piece of material.

2. The wound pad of claim 1, wherein each of the plurality of separable layers includes an edge and the first region is disposed adjacent the edge.

3. The wound pad of claim 1, wherein each of the plurality of separable layers has a layer width, and the layer width of each of the plurality of separable layers is substantially the same as the pad width.

4. The wound pad of claim 1, wherein each of the plurality of separable layers includes only one first region.

5. The wound pad of claim 1, wherein each of the plurality of separable layers has a layer length, and the layer length of each of the plurality of separable layers is substantially the same as the pad length.

6. The wound pad of claim 1, wherein at least one of the plurality of separable layers includes only one first region.

7. The wound pad of claim 1, wherein:
    each of the plurality of separable layers has a layer length and a layer width;
    the layer width of each of the plurality of separable layers is substantially the same as the pad width; and
    the layer length of each of the plurality of separable layers is substantially the same as the pad length.

8. The wound pad of claim 1, wherein:
    each of the plurality of layers has a third region unconnected from any adjacent layer; and
    within each of the plurality of layers, the first region is disposed between the second and third regions.

9. The wound pad of claim 8, wherein the first region of each of the plurality of layers is disposed within a middle third lengthwise of the wound pad.

10. The wound pad of claim 9, wherein the first region of each of the plurality of layers is disposed at a center lengthwise of the wound pad.

11. The wound pad of claim 1, wherein each of the plurality of separable layers is configured to maintain the layer width, layer length, and layer thickness when connected to the at least one adjacent layer and when disconnected from the at least one adjacent layer.

12. The system of claim 11, wherein the wound pad comprises a polyurethane foam.

13. The wound pad of claim 1, comprising an open-cell foam.

14. The wound pad of claim 13, comprising a polymer foam.

15. The wound pad of claim 14, wherein the polymer foam comprises polyurethane foam, polyvinyl alcohol foams, silicone foams, polyolefin foams, alginate foams, or combinations thereof.

16. The wound pad of claim 15, wherein the polymer foam comprises polyurethane foam.

17. The wound pad of claim 16, wherein the polyurethane foam is a polyester-based foam, a polyether-based foam, or a combination thereof.

18. The wound pad of claim 17, wherein the polymer foam is hydrophobic.

19. The wound pad of claim 18, wherein the polymer foam is hydrophilic.

20. The wound pad of claim 1, wherein the first region of each of the plurality of layers is disposed within a middle third lengthwise and within a middle third widthwise of the wound pad.

21. The wound pad of claim 1, wherein, within each of the plurality of layers, the first region is surrounded by the second region.

22. A system for the treatment of a wound using negative pressure, comprising:
    a negative pressure source for providing negative pressure to the wound;
    a conduit configured to transmit negative pressure from the negative pressure source to the wound; and
    a wound pad suitable for use as a wound filler comprising an open-cell foam and including a pad thickness, a pad width, and a pad length, the pad thickness being less than the pad width and less than the pad length, the wound pad further including a plurality of separable layers, each of the plurality of separable layers having a layer length and a layer width, the layer width of each of the plurality of separable layers being substantially the same as the pad width and the layer length of each of the plurality of separable layers being substantially the same as the pad length;
    wherein each separable layer includes a first region connected to at least one adjacent separable layer and a second region unconnected from any adjacent separable layer, and
    wherein the plurality of separable layers are constructed from a single piece of material.

23. A wound pad having a pad width, a pad length, and a pad thickness, wherein the pad thickness is less than the pad width and less than the pad length, comprising:
    a first separable layer,
    a second separable layer adjacent to the first separable layer on a first side of the second separable layer, and a third separable layer adjacent to the second separable layer on a second side of the second separable layer opposite to the first side of the second separable layer,
each separable layer having:
  a layer thickness that is less than the pad thickness,
  a layer width that is substantially the same as the pad width, and
  a layer length that is substantially the same as the pad length,
wherein the first separable layer comprises:
  a first region connected to the second separable layer,
  a second region unconnected to the second separable layer, and
  a third region unconnected to the second separable layer,
wherein the third separable layer comprises:
  a first region connected to the second separable layer,
  a second region unconnected to the second separable layer, and
  a third region unconnected to the second separable layer,
wherein the first region of the first separable layer is disposed between the second and third regions of the first separable layer;
wherein the first region of the third separable layer is disposed between the second and third regions of the third separable layer;
wherein the first, second, and third separable layers comprise an open-cell foam,
wherein the first, second, and third separable layers are configured to be removed from each other,
wherein removal of a single one of the first, second, and third separable layers from the remainder ones of the first, second, and third separable layers reduces the pad thickness, and
wherein the first, second, and third separable layers are constructed from a single piece of material.

24. The wound pad of claim 23, wherein the first, second, and third separable layers comprise polyurethane foam.

* * * * *